US008961473B2

(12) United States Patent
Heald

(10) Patent No.: US 8,961,473 B2
(45) Date of Patent: Feb. 24, 2015

(54) DRIVE MECHANISM FOR A DRUG DELIVERY DEVICE AND DRUG DELIVERY DEVICE

(71) Applicant: Sanofi-Aventis Deutschland GmbH, Frankfurt am Main (DE)

(72) Inventor: Michael Heald, Crewe (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/947,259

(22) Filed: Jul. 22, 2013

(65) Prior Publication Data

US 2013/0317452 A1 Nov. 28, 2013

Related U.S. Application Data

(63) Continuation of application No. 13/702,818, filed as application No. PCT/EP2011/059575 on Jun. 9, 2011, now abandoned.

(30) Foreign Application Priority Data

Jun. 11, 2010 (EP) .................................... 10165646

(51) Int. Cl.
*A61M 5/00* (2006.01)
*A61M 5/315* (2006.01)
(52) U.S. Cl.
CPC ......... *A61M 5/31545* (2013.01); *A61M 5/3155* (2013.01); *A61M 5/31583* (2013.01)
USPC .......................................... 604/207; 604/246
(58) Field of Classification Search
USPC ........................................................ 604/207
See application file for complete search history.

(56) References Cited

U.S. PATENT DOCUMENTS 5,827,232 A * 10/1998 Chanoch et al. ............... 604/208
(Continued)

FOREIGN PATENT DOCUMENTS

| EP | 1923085 | 5/2008 |
| WO | 99/38554 | 8/1999 |

OTHER PUBLICATIONS

International Search Report for Int. App. No. PCT/EP2011/059575, completed Aug. 29, 2011.
(Continued)

Primary Examiner — Jason Flick
(74) Attorney, Agent, or Firm — McDonnell Boehnen Hulbert & Berghoff LLP

(57) ABSTRACT

A drive mechanism for a drug delivery device comprises a housing having a proximal end and a distal end and a piston rod, which is adapted to be displaced in a distal direction with respect to the housing when dispensing a drug dose. A drive member is adapted to be rotated when dispensing the drug dose, wherein the drive mechanism is configured to convert rotational movement of the drive member into a movement of the piston rod in the distal direction with respect to the housing. A stop member is adapted to prevent a rotational movement of the drive member with respect to the housing when setting a drug dose. The drive member comprises a drive portion being coupled to the piston rod and a first coupling portion which couples the drive portion and the stop member, wherein the drive mechanism is configured to be switchable between a set and dispense mode of operation and a reset mode of operation, and wherein, in the set and dispense mode, said first coupling portion is bi-directionally coupled to the drive portion for setting and dispensing the drug dose, and wherein, in the reset mode, said first coupling portion is decoupled from the drive portion to allow a reset operation to be performed for the drive mechanism.

17 Claims, 4 Drawing Sheets

(56) References Cited

U.S. PATENT DOCUMENTS

2006/0153693 A1    7/2006  Fiechter et al.
2007/0123829 A1*   5/2007  Atterbury et al. ............. 604/207
2009/0275914 A1*  11/2009  Harms et al. .................. 604/506

OTHER PUBLICATIONS

International Preliminary Report on Patentability for PCT/EP2011/059575, mailed Dec. 27, 2012.

* cited by examiner

DRIVE MECHANISM FOR A DRUG DELIVERY DEVICE AND DRUG DELIVERY DEVICE

CROSS REFERENCE TO RELATED APPLICATIONS

The present application is a continuation of U.S. patent application No. 13,702,818, filed Dec. 7, 2012, which is a U.S. National Phase Application pursuant to 35 U.S.C. §371 of International Application No. PCT/EP2011/059575 filed Jun. 9, 2011, which claims priority to European Patent Application No. 10165646.0 filed on Jun. 11, 2010. The entire disclosure contents of these applications are herewith incorporated by reference into the present application.

FIELD OF INVENTION

The present disclosure relates to a drive mechanism for a drug delivery device and a drug delivery device incorporating such a drive mechanism.

BACKGROUND

In a drug delivery device, a piston within a cartridge that contains drug may be displaced with respect to the cartridge in the distal direction by a piston rod which moves in the distal direction with respect to the cartridge. Thereby, a dose of drug can be expelled from the cartridge. A drug delivery device is described in US 2007/0123829 A1, for example.

It is often desirable that the actually delivered dose of drug matches the dose which was previously set by a user or which the device was designed to deliver as close as possible, i.e. dose accuracy should be good.

SUMMARY

It is an object to provide a novel drive mechanism, in particular a drive mechanism that facilitates provision of an improved drug delivery device, for example a device with good dose accuracy. Furthermore, a novel, in particular an improved, drug delivery device should be provided.

This object may be achieved by a drive mechanism according to the independent claim. Further features, advantages and expediencies are subject matter of the dependent claims.

According to an aspect, a drive mechanism for a drug delivery device comprises a housing having a proximal end and a distal end, and a piston rod, which is adapted to be displaced in a distal direction with respect to the housing when dispensing the dose. A drive member is adapted to be rotated with respect to the housing during setting and dispense of a dose of a drug, wherein a drive mechanism of the drive member is adapted to convert rotational movement of the drive member into a, preferably lateral, movement of the piston rod in the distal direction with respect to the housing.

A stop member is adapted to prevent and preferably prevents rotational movement of the drive member with respect to the housing during setting of the dose. The drive member may comprise a drive portion, said drive portion being coupled to the piston rod and a first coupling portion, which couples the drive portion and the stop member. The drive mechanism is configured to be switchable between a set and dispense mode of operation and a reset mode of operation. In the set and dispense mode, the first coupling portion is bi-directionally coupled, preferably bi-directionally rotationally coupled, to the drive portion for setting and dispensing the dose. In the reset mode, the first coupling portion is decoupled from the drive portion, thereby allowing a reset operation of the drive portion to be performed for the drive mechanism.

Mechanical interaction of stop member and drive member, for example interlocking, engagement, and/or abutment, during rotation of the rotation member in the first direction may prevent rotational movement of the drive member with respect to the housing in the first direction and, in particular, with respect to the stop member during setting of the dose. Thus, rotation of the drive member during dose setting can be avoided. The drive member may be coupled to the piston rod by its drive portion, so as to convert its rotational movement in the second direction into distal movement of the piston rod with respect to the housing. The drive member may (also) be coupled to the piston rod by its drive portion so as to convert its rotational movement in the first direction with respect to the housing into proximal movement of the piston rod with respect to the housing. Accordingly, the risk of the piston rod being moved in the proximal direction during dose setting can be reduced by preventing rotational movement of the drive member in the first direction during setting of the dose due to provision of the stop member. Unintentional proximal movement of the piston rod may result in decreased dose accuracy. Consequently, dose accuracy may be improved by preventing (any) rotation of the drive member with respect to the housing during dose setting.

For switching into the reset mode of operation, the drive portion may be mechanically decoupled from the first coupling portion and, thus, from the stop member, such that a reset of the piston rod which is coupled to the drive member, preferably only, via its drive portion can be achieved. The term "bi-directional" coupling between the first portion and the drive portion preferably indicates that the portions are rotationally locked when they are bi-directionally coupled, i.e. they rotate together. On the other hand, axial movement may still be possible.

In an embodiment, the first coupling portion is coupled to the stop member by a uni-directional clutch mechanism, preferably a friction clutch mechanism. The uni-directional clutch mechanism is configured to prevent relative rotational movement between the stop member and the first coupling portion during setting of the drug dose. However, it permits relative rotational movement between the stop member and the first coupling portion when dispensing the dose.

In another embodiment, the first coupling portion and the drive portion each comprise an interlocking element. The interlocking elements preferably face each other. The interlocking elements are, in the set and dispense mode of operation, expediently adapted and arranged to cooperate with each other, preferably by engaging one another, to rotationally lock the drive portion and the first coupling portion with one another. In the reset mode, the interlocking elements are preferably disengaged to allow relative rotational movement of the drive portion with respect to the first coupling portion, which may still be coupled to the stop member via the uni-directional clutch in the reset mode.

In another embodiment, a first resilient member is arranged between the first coupling portion and the drive portion. The first resilient member is preferably adapted to axially displace one of the first coupling portion and the drive portion with respect to the other one, in particular so as to disengage the interlocking elements. By the resilient member the first coupling portion is decoupled from the drive portion during reset operation. Consequently, the drive portion can still interact with the piston rod during reset mode. The drive portion may be permanently engaged with the piston rod. The drive portion may be locked rotationally but may be moved axially.

The first coupling portion is preferably permanently, e.g. in the set and dispense mode and in the reset mode, decoupled from the piston rod.

In another embodiment, the drive mechanism comprises a rotation member adapted to be rotated in a first direction when setting a dose and adapted to rotate in a second direction when dispensing the previously set dose. First and second direction may be opposite to each other. The drive member may follow the rotational movement of the rotation member when dispensing the drug dose. Rotation of the drive member in that direction in which the rotation member rotates during dose setting may be prevented on account of the stop member mechanically cooperating with the drive member, in particular despite a frictional contact between rotation member and drive member.

In another embodiment, the first coupling portion is arranged between the drive portion and the stop member.

In another embodiment, the drive member comprises a second coupling portion. The second coupling portion may be arranged between the drive portion and the rotation member. In the set and dispense mode, the second coupling portion is bi-directionally coupled, preferably bi-directionally rotationally coupled, to the drive portion. It may be displaced with respect to and disengaged from the drive portion in the reset mode of the drive mechanism. As a result, the drive portion may be freely rotated in the reset mode as it is decoupled from both coupling portions.

The piston rod may be decoupled from both coupling portions in the set and dispense mode as well as in the reset mode. The only coupling between piston rod and drive member may be effected via the drive portion.

In another embodiment, the drive member is coupled to the rotation member by a uni-directional clutch mechanism, preferably a friction clutch mechanism. The clutch mechanism may be configured to permit relative rotational movement between the rotation member and the drive member during rotation of the rotation member in the first direction for setting the drug dose. The clutch mechanism may prevent relative rotational movement of the rotation member and the drive member during rotation of the rotation member in the second rotational direction when dispensing the dose.

In another embodiment, the second coupling portion and the drive portion each comprise an interlocking element. The interlocking elements preferably face each other. The interlocking elements are, in the set and dispense mode of operation, expediently adapted and arranged to cooperate with each other, preferably by engaging one another, to rotationally lock the drive portion and the second coupling portion with one another. In the reset mode, the interlocking elements are preferably disengaged to allow relative rotational movement of the drive portion with respect to the second coupling portion, which may still be coupled to the rotation member via the uni-directional clutch in the reset mode.

Thus, the drive member may have a plurality of parts, e.g. the drive portion for interacting with the piston rod, the first coupling portion to interact with the stop member, and preferably the second coupling portion to interact with the rotation member. The drive portion is releaseably coupled to the respective coupling portion. When the parts of the drive member are coupled, they may act as one. When they are decoupled, relative movement between the drive portion and the first coupling portion, in particular rotation of the drive portion with respect to the respective coupling portion, is permitted.

In another embodiment, a second resilient member can be arranged between the second coupling portion and the drive portion. The second resilient member is preferably adapted to axially displace one of the second coupling portion and the drive portion with respect to the other one, in particular so as to disengage the interlocking elements. By the second resilient member the second coupling portion is decoupled from the drive portion during reset operation. Consequently, the drive portion can still interact with the piston rod in the reset mode. The drive portion may be permanently engaged with the piston rod, locked rotationally but will move axially. The second coupling portion is preferably permanently, e.g. in the set and dispense mode and in the reset mode, decoupled from the piston rod.

Both resilient members may exert an axially directed force onto the drive portion and the respective coupling portion to push the portions apart when the drive mechanism is reset.

In another embodiment, the respective resilient member or both resilient member comprise at least one of the following:
a coil spring,
a wave spring,
a wavy washer,
an elastomeric component,
a metal component,
a plastic hinge.

The respective resilient member exerts a force, preferably an axial force, when it is deformed, e.g. compressed. In the set and dispense mode, the respective resilient member may be deformed. The corresponding force may tend to decouple the drive portion and the respective coupling portion in the set and dispense mode. However, the drive portion and the respective coupling portion are expediently kept coupled in the set and dispense mode. For this purpose, the force exerted by the resilient members is expediently balanced or overcome by an element fixed to the housing and/or by a further resilient element in the set and dispense mode. In the reset mode the force is no longer balanced or overcome and thus the force decouples the drive portion and the respective coupling portion. For this purpose, the element which was previously fixed to the housing may be detached from the housing and/or the force exerted by the resilient element onto the resilient members may be reduced.

Instead of providing a separate resilient member, the respective resilient member may be integrated into the drive portion or the respective coupling portion.

In another embodiment, the drive mechanism comprises a resilient element, exerting an axially directed force onto the stop member and the drive member to hold them in abutment when setting and dispensing the drug dose. The force exerted by this resilient element may be stronger than a force exerted by the first and second resilient elements in the set and dispense mode of the drive mechanism. Accordingly, the force exerted by the first and second resilient members which tends to separate the drive portion and the respective coupling portion may be overcome by the resilient element. Thus, the drive portion and the respective coupling portion are kept bi-directionally coupled in the set and dispense mode.

In another embodiment, the stop member and/or the rotation member is movable in axial direction with respect to the housing in the reset mode of the drive mechanism or when switching the drive mechanism into reset mode.

In another embodiment, the piston rod is displaced in the distal direction with respect to the housing along the rotation axis of the drive member or the rotation member, respectively. The rotation axis may run along the piston rod and, in particular, along a main direction of extent of the piston rod. The piston rod may be splined or rotationally locked to the drive member. The piston rod may be threadedly coupled to the housing to convert rotational movement of the piston rod into (axial) displacement of the piston rod with respect to the housing.

In another embodiment, the drive mechanism comprises a dose member. The dose member is preferably movable with respect to the housing during setting and/or delivery of the dose. The dose member may be movable in the proximal direction with respect to the housing for setting the dose. The dose member may be movable in the distal direction with respect to the housing for delivering the set dose. Movement of the dose member with respect to the housing may be converted into rotational movement of the rotation member with respect to the housing. Movement of the dose member for setting the dose may be converted into rotational movement of the rotation member with respect to the housing in the first direction. Movement of the dose member for delivering the set dose may be converted into rotational movement of the rotation member with respect to the housing in the second direction. The dose member may be secured against rotational movement with respect to the housing. The dose member may be splined to the housing, for example. The dose member may be movable with respect to the rotation member.

In another embodiment, the dose member and the rotation member are engaged, preferably threadedly engaged and/or permanently engaged. Rotational movement of the rotation member may be achieved by the (threaded) engagement which may convert (linear) movement of the dose member into rotational movement of the rotation member with respect to the housing.

Features which are described herein above and below in connection with the drive mechanism may also be applied for the corresponding drug delivery device and vice versa.

Further features, refinements and expediencies become apparent from the following description of the exemplary embodiments in connection with the figures.

BRIEF DESCRIPTION OF THE FIGURES

Like elements, elements of the same kind and identically acting elements may be provided with the same reference numerals in the figures.

DETAILED DESCRIPTION

Figure 1:
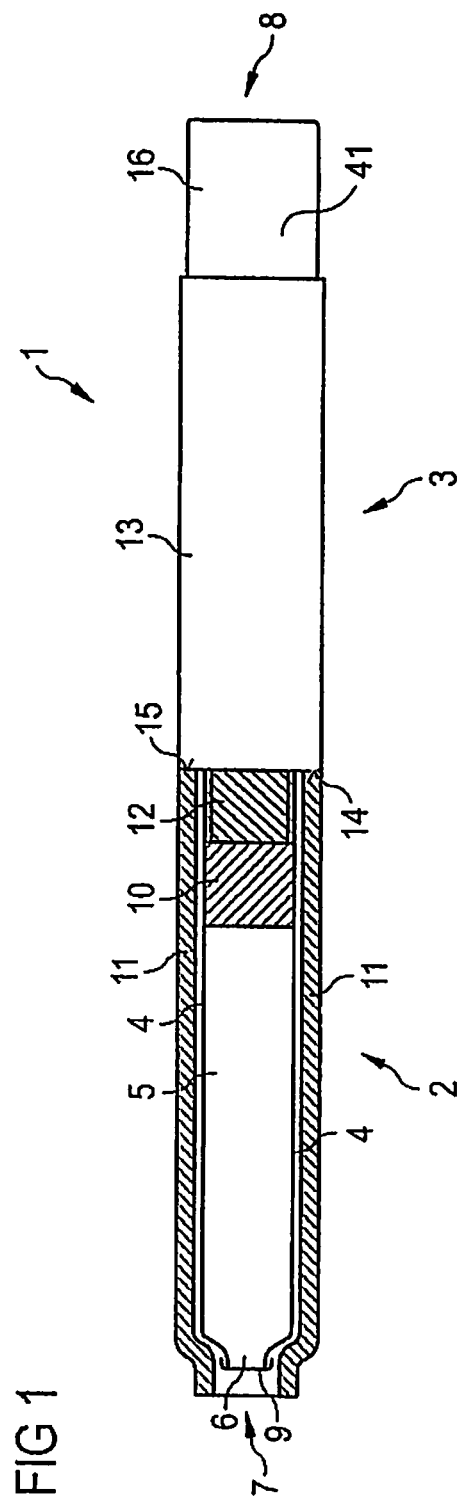
FIG. 1 schematically shows a partly sectional side view of an exemplary embodiment of a drug delivery device.

Turning now to FIG. 1, a drug delivery device 1 comprises a cartridge unit 2 and a drive unit 3. The cartridge unit 2 comprises a cartridge 4. Drug 5 is retained in the cartridge 4. The drug 5 is preferably liquid drug. The cartridge 4 preferably comprises a plurality of doses of the drug 5.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl -ThrB29LysB30 human insulin; B30-N-palmitoyl -ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39), des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5-des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(0)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The cartridge 4 has an outlet 6 at its distal end. Drug 5 can be dispensed from the cartridge through outlet 6. The device 1 may be a pen-type device, in particular a pen-type injector. The device 1 may be a disposable or a reusable device. The device 1 may be a device configured to dispense fixed doses of the drug or variable, preferably user-settable, doses. The device 1 may be a needle-based or a needle free device and may be an injection device.

The term "distal end" of the drug delivery device 1 or a component thereof may refer to that end of the device or the component which is closest to the dispensing end of device 1. The term "proximal end" of the drug delivery device 1 or a component thereof may refer to that end of the device or the component which is furthest away from the dispensing end of the device. In FIG. 1, the distal end of the device 1 was assigned reference numeral 7 and the proximal end of the device was assigned reference numeral 8.

The outlet 6 may be covered by a membrane 9, which protects drug 5 against external influences during storage of the cartridge. For drug delivery, membrane 9 may be opened, e.g. pierced. For example, membrane 9 may be pierced by a needle unit (not explicitly shown). The needle unit may be (releasably) attached to the distal end of the cartridge unit 2. The needle unit may provide for fluid communication from the inside of cartridge 4 to the outside of the cartridge through outlet 6.

A piston 10 is retained within cartridge 4. Piston 10 is movable with respect to the cartridge and may seal the drug 5 within the cartridge. The piston 10 expediently seals the interior of the cartridge 4 proximally. Movement of piston 10 with respect to cartridge 4 in the distal direction causes drug 5 to be dispensed from the cartridge through outlet 6 during operation of the device.

The cartridge unit 2 furthermore comprises a cartridge retaining member 11. The cartridge 4 is retained within cartridge retaining member 11. The cartridge retaining member 11 may stabilize cartridge 4 mechanically. Additionally or alternatively, cartridge retaining member 11 may be provided with a fixing member (not explicitly shown) for attaching cartridge unit 2 to drive unit 3.

The cartridge unit 2 and drive unit 3 are secured to one another, preferably releasably secured. A cartridge unit 2 which is releasably secured to the drive unit may be detached from drive unit 3, for example in order to allow for providing for a new cartridge 4, if all of the doses of drug which once were in the cartridge formerly attached to the drive unit 3 have been dispensed. The cartridge retaining member 11 may be releasably secured to drive unit 3 via a thread.

Alternatively, cartridge retaining member 11 may be dispensed with. It is particularly expedient, in this case, to apply a robust cartridge 4 and to attach the cartridge directly to drive unit 3.

The drive unit 3 is configured for transferring force, preferably user-exerted force, particularly preferably manually exerted force, to piston rod 12 for displacing piston 10 with respect to cartridge 4 in the distal direction. By this displacement, a dose of drug is dispensed from the cartridge. The size of the delivered dose is determined by the distance by which piston 10 is displaced with respect to cartridge 4 in the distal direction.

The drive unit 3 comprises a drive mechanism. The drive mechanism comprises a piston rod 12. The piston rod 12 may be configured for transferring force to piston 10, thereby displacing the piston in the distal direction with respect to cartridge 4. A distal end face of piston rod 12 is arranged to abut a proximal end face of piston 10. A bearing member (not explicitly shown) may be arranged to advance the piston 10, preferably to abut the proximal end face of the piston 10. The bearing member may be arranged between piston 10 and piston rod 12. The bearing member may be fixed to piston rod 12 or a separate member. If piston rod 12 is configured to be rotated during operation of the device, for example during dose delivery, it is particularly expedient to provide for a bearing member. The bearing member may be displaced together with the (rotating) piston rod with respect to the housing. The piston rod may be rotatable with respect to the bearing member. In this way, the risk that the rotating piston rod drills into the piston and thereby damages the piston is reduced. Accordingly, while the piston rod rotates and is displaced with respect to the housing, the bearing member is preferably only displaced, i.e. does not rotate. The piston rod may be bounded by the bearing member.

The drive unit 3 also comprises a housing 13 which may be part of the drive mechanism and in which piston rod 12 is retained. A proximal end side 14 of the cartridge unit 2 may be secured to the drive unit 3 at a distal end side 15 of the housing 13, for example via a threaded connection. Housing 13, cartridge 4 and/or cartridge retaining member 11 may have a tubular shape.

The term "housing" shall preferably mean any exterior housing ("main housing", "body", "shell") or interior housing ("insert", "inner body") which may have a unidirectional axial coupling to prevent proximal movement of specific components. The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, piston, piston rod), preferably by limiting the exposure to contaminants, such as liquid, dust, dirt etc. In general, the housing may be unitary or a multipart component of tubular or non-tubular shape.

The term "piston rod" shall preferably mean a component adapted to operate through/within the housing, which may be designed to transfer axial movement through/within the drug delivery device, preferably from the drive member to the piston, for example for the purpose of discharging/dispensing an injectable product. Said piston rod may be flexible or not. It may be a simple rod, a lead-screw, a rack and pinion system, a worm gear system, or the like. "piston rod" shall further mean a component having a circular or non-circular cross-section. It may be made of any suitable material known by a person skilled in the art and may be of unitary or multipart construction.

The drive unit 3 comprises a dose part 16. The dose part 16 is movable with respect to the housing 13. The dose part 16 may be movable in the proximal direction with respect to the housing for setting of a dose of the drug 5 which is to be delivered and in the distal direction with respect to the housing for delivery of the set dose. The dose part 16 is preferably connected to the housing 13. The dose part 16 may be secured against rotational movement with respect to the housing. The dose part 16 may be moved (displaced) between a proximal end position and a distal end position with respect to the housing 13 (not explicitly shown). The distance by which the dose part is displaced with respect to the housing during setting of the dose may determine a size of the dose. The proximal end position and the distal end position may be determined by a respective stop feature which may limit the proximal or distal travel of the dose member with respect to the housing. The device 1 may be a variable dose device, i.e. a device configured for delivering doses of drug of different, preferably user-settable, sizes. Alternatively, the device may be a fixed dose device.

Device 1 in the present embodiment is a manually, non-electrically, driven device. The (user-applied) force which causes dose part 16 to be moved with respect to housing 13 in the distal direction may be transferred to piston rod 12 by the drive mechanism. For this purpose, other elements of the drive mechanism may be provided which are not explicitly shown in FIG. 1. The drive mechanism is preferably configured not to move piston rod 12 with respect to housing 13 when the dose part is moved in the proximal direction with respect to the housing for setting of the dose.

Embodiments of a drive mechanism which are suitable to be provided in the drug delivery device 1 as it was described above are described in more detail below.

An embodiment of a drive mechanism which is suitable for being implemented in the drug delivery device 1 as described above is described in connection with FIGS. 2 to 7.

The drive mechanism comprises a housing part 17. The housing part 17 has a proximal end 18 and a distal end 19. The housing part 17 may be (outer) housing 13 of FIG. 1, a part thereof or an insert within housing 13, which insert is preferably secured against rotational and axial movement with respect to housing 13. Housing part 17 may be an insert sleeve, for example. The insert sleeve may be snap-fitted or glued to housing 13, for example. The housing part 17 may have a tubular shape.

Piston rod 12 is retained in housing 13 and preferably within housing part 17. The piston rod 12 is driven in the distal direction with respect to housing part 17 during dose delivery.

Figure 6:
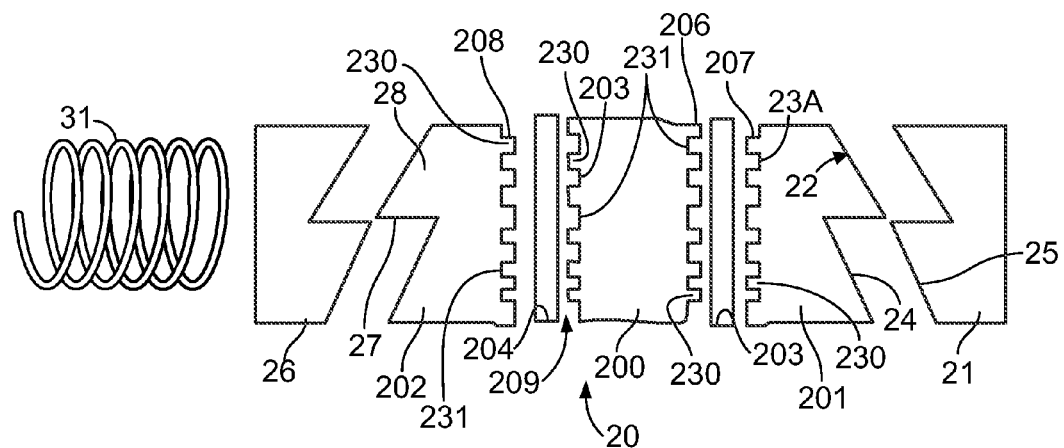
FIG. 6 schematically shows a explosive view of the drive mechanism that is configured in accordance with the first embodiment.

The drive mechanism furthermore comprises drive member 20 comprising several portions, which are explained in greater detail in FIG. 6.

Drive member 20 is retained within housing part 17 and configured to transfer force, preferably torque, to piston rod 12 and may engage piston rod 12. The transferred force may cause the piston rod 12 to be displaced in the distal direction with respect to the housing part 17 for dose delivery. Drive member 20 is rotatable with respect to housing part 17. Rotational movement of the drive member, for example rotational movement in a second direction may be converted into distal movement of the piston rod 12 with respect to the housing part 17. This is explained in more detail below.

The drive mechanism furthermore comprises a rotation member 21. The rotation member 21 is rotatable with respect to the housing part 17 in a first direction, in particular for setting of a dose of the drug, and in a second direction, in particular for delivering the set dose. The second direction is opposite to the first direction. The first direction may be counter-clockwise and the second direction may be clockwise as seen from the proximal end of the device, for example.

Drive member, rotation member and/or piston rod are preferably configured to be rotatable about a (common) rotation axis. The rotation axis may extend through drive member, rotation member and/or piston rod. The rotation axis may be the main longitudinal axis of the piston rod. The rotation axis may run between the proximal end and the distal end of the housing part 17.

The rotation member 21 is coupled to drive member 20 by an uni-directional clutch mechanism, in particular a friction clutch mechanism. This clutch mechanism permits rotational movement of rotation member 21 with respect to drive member 20 when the rotation member rotates in the first direction with respect to housing part 17. The clutch mechanism prevents rotational movement of rotation member 21 with respect to drive member 20, when the rotation member rotates in the second direction with respect to housing part 17. The drive member 20 may thus follow rotational movement of rotation member 21 in the second direction with respect to housing part 17.

The drive member 20 is arranged to abut and/or engage the rotation member and, in particular, engages rotation member 21. The drive member 20 comprises a teeth 22. Teeth 22 may be provided at one end of the drive member, e.g. its proximal end. The rotation member comprises a teeth 23. Teeth 22 and 23 face one another. Teeth 23 may be provided at one end of the rotation member which end faces the drive member 20, e.g. at the distal end of the rotation member. Teeth 22 comprises a plurality of teeth 24. Teeth 23 comprises a plurality of teeth 25. Teeth 24 and/or 25 may extend and preferably may be oriented along the rotation axis. Teeth 22 and 23 may be configured to mate with one another. The rotation member and the drive member may engage each other by teeth 22 and 23 being in engagement.

A respective tooth of teeth 24 and/or teeth 25 may be ramp-shaped, in particular along the azimuthal (angular) direction as seen from the rotation axis. The ramp of the respective tooth is limited (in the angular direction) by a steep end face of that tooth, i.e. a face of the tooth that runs parallel to the rotation axis or includes a smaller angle with the rotation axis when projected on this axis than the ramp when projected on this axis. The steep end face is followed by the ramp of the next tooth.

The teeth 24 may be circumferentially disposed on the drive member 20, particularly at the end of the drive member 20 which faces the rotation member 21. The teeth 25 may be circumferentially disposed on the rotation member 21, particularly at the end of the rotation member 21 which faces the drive member 20.

When the steep end faces of two teeth abut and the rotation member is rotated further on in the second direction, the steep sides stay in abutment and drive member 20 follows the rotation of rotation member 21. When the rotation member rotates in the first direction, the ramp of the teeth—which ramps, in particular, run obliquely with respect to the rotation axis—slide along each other and, in consequence, rotation member 21 may rotate with respect to drive member 20.

The drive mechanism furthermore comprises a stop member 26. The drive member may be arranged between stop member 26 and rotation member 21. Stop member 26 is configured for preventing rotational movement of drive member 20 in the first direction with respect to housing part 17 during setting of a dose, i.e. when the rotation member rotates in the first direction. Thus, rotation member 21 may rotate in the first direction with respect to housing part 17, whereas drive member 20 and stop member 21 do not rotate. The stop member 26 is coupled to drive member 20 by another uni-directional clutch mechanism, in particular a friction clutch mechanism. This clutch mechanism prevents rotational movement of drive member 20 with respect to stop member 26 when the rotation member rotates in the first direction with respect to housing part 17. The clutch mechanism permits rotational movement of drive member 20 with respect to stop member 26, when the rotation member rotates in the second direction with respect to housing part 17.

Thus, the rotation member 21 may rotate with respect to the drive member 20 and the stop member 26 in the first direction during setting of the dose, with rotation of the drive member being prevented by its interaction with the stop member, and rotation member as well as drive member may rotate with respect to the stop member in the second direction during delivery of the dose.

The stop member may be arranged to abut and/or engage the drive member during setting of the dose and, preferably, during delivery of the dose. The stop member 26 is provided with teeth 27 on that side of the stop member 26 which faces the drive member 20. The teeth 27 may be ramp-shaped with a steep side and a less steep ramp. The teeth 27 may be disposed azimuthally along the perimeter of the stop member 26. The teeth 27 may extend and preferably may be oriented along the rotation axis.

The drive member 20 is provided with teeth 28 on that side of the drive member 20 which faces the stop member 26. The teeth 28 may extend and preferably be oriented along the rotation axis. The teeth 24 and the teeth 28 of the drive member 20 are oppositely disposed. The teeth 24 may be configured corresponding to the teeth 25 of the rotation member 21. The teeth 28 may be configured corresponding to the teeth 27 of the stop member 26. The teeth 27 and 28 may face one another and may especially mate with one another. The teeth 27 and 28, in particular the steep sides of the teeth, cooperate, e.g. abut, for preventing rotation of the drive member 20 with respect to the housing part 17 and, in particular, with respect to the stop member 26 in the first direction.

Stop member 26 is preferably secured against rotational movement, particularly preferably permanently secured against rotational movement, with respect to the housing part 17. For this purpose, it may be fixed to the housing or integrated into the housing. Stop member 26 may be fixed against displacement with respect to the housing part 17 or displacement with respect to the housing part 17 may be allowed.

As it is illustrated in the present embodiment, stop member 26 is displaceable with respect to the housing but non-rotatable with respect to the housing part 17. For that purpose, one or a plurality of, preferably oppositely disposed, guide features, for example guide lugs 29, are provided in the stop member 26. The respective guide feature 29 engages a corresponding guide slot 30 which may be provided in the housing, e.g. in housing part 17. This can be seen in FIGS. 2 to 5. A guide feature 29 cooperates with a guide slot 30 to prevent rotational movement of the stop member with respect to the housing part 17, with axial movement of the stop member 26 with respect to the housing being allowed. The axial movement of the stop member 26 may compensate for play between components of the drive mechanism during operation.

From the group comprising drive member 20, stop member 26 and rotation member 21 one or more members, preferably two members or three members, may be axially displaceable with respect to the housing part 17 and, preferably, with respect to the piston rod 12. Therein, the drive member and another one of the recited members may be axially displaceable with respect to the housing. The remaining member may be secured against axial displacement or may also be axially displaceable during operation of the drive mechanism for drug delivery. Accordingly, if the drive member and the stop member are axially displaceable, the rotation member may be axially secured or axially displaceable and so on. Play between the components caused by relative (axial) movement of components of the clutch mechanism with respect to the housing can be compensated for in this way. The distance by which the respective components may be axially displaced with respect to the housing may correspond to the (maximum) depth of a tooth of the respective teeth 22 or 28 of the drive member. Alternatively, the distance may be greater than the (maximum) depth of a tooth of the respective teeth.

Furthermore, the drive mechanism comprises a resilient member 31, preferably a spring member. The resilient member 31 may be biased during drug delivery operation of the drive mechanism. The resilient member may provide for a force that tends to keep drive member 20 in engagement with stop member 26 and/or rotation member 21 during setting and dispensing a drug dose. The force may be exerted along the rotation axis. In the situation shown in FIGS. 2 to 5, this force may be exerted in the proximal direction. The resilient member 31 may be a helical (coil) spring. The resilient member 31 may be a compression spring.

The resilient member 31 may keep the drive member 20 and the stop member 26 in mechanical contact, e.g. in abutment, with each other during setting and delivery of a dose of the drug. Alternatively or additionally, the resilient member 31 may keep the drive member 20 and the rotation member 21 in mechanical contact, preferably abutment, with each other during setting and delivery of a dose of the drug. In a reset mode, however, the resilient member 31 is relaxed, such that drive member 20 is disengaged from stop member 26 and/or from rotation member 21. In this mode, drive member 20, being in contact with piston rod 12 is now able to rotate in both directions. The drive mechanism may now be reset by, for example rotate the piston rod 12 back to its initial position.

The resilient member 31 may be integrated within stop member 26 or a separate component. The resilient member 31 may be arranged on the distal end side of the stop member 26.

The drive mechanism furthermore comprises a support member 32. Support member 32 is expediently fixed against axial and rotational movement with respect to the housing part 17 or integrated into housing part 17. Support member 32 is arranged on that side of drive member 20 which is remote from stop member 26. Support member 32 may be a protrusion, for example a ring-like protrusion. Rotation member 21 extends through an opening in support member 32, while support member 32 provides for a counter force to the force which is exerted by resilient member 31. Abutment of the rotation member with the drive member and of the drive member with the stop member during setting and delivery of drug is facilitated in this way.

The rotation member 21 has an (radially) outwardly protruding member 33, for example a flange portion. The protruding member 33 is expediently provided for abutting support member 32, in particular the distal end side of support member 32.

Another support (not illustrated here) is provided for providing a counterforce to the force exerted by the resilient member 31. This support is arranged on that side of the drive member 20 which is remote from the rotation member 21 and also remote from the support member 32. The support may be arranged to abut the resilient member 31. The support may be secured against axial and rotational movement with respect to the housing part 17, with respect to the housing 13 or integrated into the housing 13 during setting and dispensing a drug. However, the support may be movable in axial direction, when the drive mechanism is reset. For instance, the support may be operable connected with retaining member 11 such that it is displaced in axial direction so to relax resilient member 31, when cartridge 4 is removed.

The drive mechanism furthermore comprises a dose member 34. Dose member 34 may be dose part 16 or may be a part of the dose part 16 of FIG. 1. Dose member 34 is movable with respect to the housing in the proximal direction for setting of a dose and for delivery of the dose. For example, the dose member 34 may be moved in the proximal direction with respect to the housing part 17 during dose setting and in the distal direction with respect to the housing part 17 during dose delivery. The dose member 34 may engage the housing part 17 or, alternatively, another part of housing 13 (not explicitly shown). Dose member 34 is preferably secured against rotational movement with respect to the housing part 17. The dose member 34 may comprise a guide feature 35, for example a guide lug or a guide slot, that engages another guide feature, for example a guide slot or a guide lug, respectively, that is provided in the housing part 17 or the housing 13. The dose member 34 may be displaced with respect to housing part 17 preferably only axially along and/or rotationally around the rotation axis.

Dose member 34 may be moved in the proximal direction and in the distal direction with respect to rotation member 21. Dose member 34 is arranged to be coupleable and is preferably (permanently) coupled to rotation member 21 such that movement of the dose member, e.g. in the proximal direction with respect to the housing part 17, for setting a dose of the drug is converted into rotational movement of the rotation member in the first direction and movement of the dose member, e.g. in the distal direction with respect to the housing part 17, for delivering the dose is converted into rotational movement of the rotation member 21 in the second direction opposite to the first direction.

The rotation member 21 may be provided with an (outer) thread 36. Thread 36 may be engaged with one of or a plurality of engagement members 42 of dose member 34. The respective engagement member may be arranged on the inside of the dose member. The respective engagement member may be a thread or a part of a thread, for example. Thus, dose member 34 and rotation member 21 may be threadedly coupled, in particularly threadedly engaged. The rotation member 21 may be arranged inside the dose member 21.

The rotation member 21, the drive member 20, the stop member 26 and/or the dose member 34 may be or may comprise a respective sleeve. The piston rod 12 may be arranged to be driven and, in particular, may be driven through one of, more of or all of those sleeves. The piston rod 12 may run through one of, more of or all of those sleeves.

The drive member 20 and the piston rod 12 are configured for rotational movement of the drive member 20 with respect to the housing being converted into rotational movement of the piston rod with respect to the housing. The drive member 20 may engage the piston rod 12. The piston rod 12 is displaceable with respect to the drive member 20 along a displacement axis. Presently, the displacement axis runs along the rotation axis. The drive member 20 may be splined to the piston rod 12, for example.

In the following, operation of the present drive mechanism for delivering drug from the cartridge 4 of FIG. 1 is described.

Figure 2:
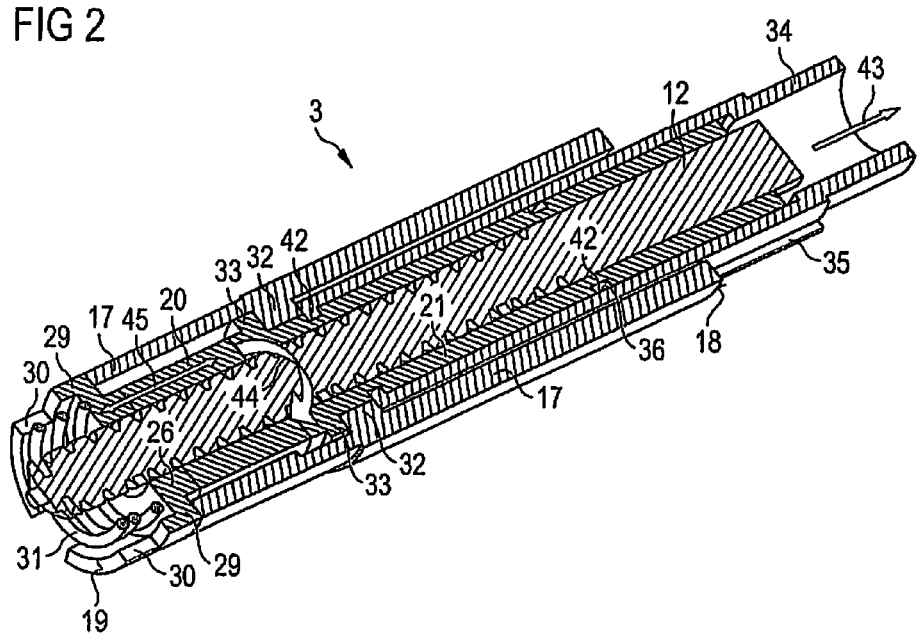
FIG. 2 schematically shows a perspective sectional view of a part of a drive mechanism according to a first embodiment with schematically indicated movements of elements thereof during setting of a dose.
Figure 3:
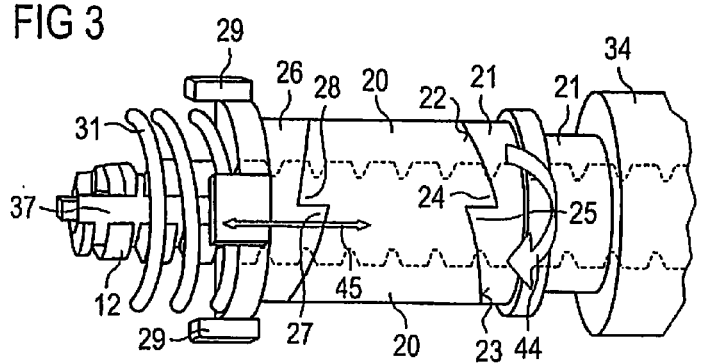
FIG. 3 schematically shows a more detailed side view of a part of FIG. 2.

To set a dose, a user may manually move dose member 34 in the proximal direction (arrow 43) with respect to the housing part 17 (cf. FIGS. 2, 3). To do so, the user may grip dose knob 41 and pull it in the proximal direction. Dose member 34 moves proximally also with respect to the rotation member 21. Proximal movement of the rotation member is prevented by support member 32 which abuts protruding member 33 of rotation member 21. Consequently, the proximal movement of dose member 34 with respect to the housing part 17 is converted into rotational movement of the rotation member 21 in the first direction (arrow 44) with respect to the housing part 17, in particular on account of the threaded engagement of dose member 34 and rotation member 21. Thus, the rotation member 21 rotates in the first direction—counter-clockwise as seen from the proximal end of the rotation member - with respect to the housing. Rotation member 21 also rotates with respect to the drive member 20 and to the stop member 26. The drive member 20 is prevented from rotating in the first direction by interaction with the stop member 26, e.g. by interlocking of teeth 27 and 28. As piston rod 12 is coupled to drive member 20 and rotation in the first direction of the drive member would cause the piston rod to travel in the proximal direction, the piston rod 12 is prevented from being driven in the proximal direction by interaction of stop member 26 and drive member 20. By preventing the piston rod 12 from moving during dose setting dose accuracy can be increased.

When the rotation member 21 rotates in the first direction, the ramps of the teeth 23 of rotation member 21 slide along the ramps of the teeth 22. Thus, a tooth of the rotation member may index around the rotation axis until the tooth engages one of the next teeth 22 of drive member 20. The teeth of rotation member 21 slide along the ramps of the teeth of drive member 20. During this movement, drive member 20 and, in particular, stop member 26 are displaced along the rotation axis with respect to piston rod 12 and housing by a distance determined by, preferably equal to, the depth of a tooth 22, before a tooth 23 (totally) disengages that tooth 22. Afterwards, the tooth of rotation member 21 engages the next tooth 22 and the force provided by resilient member 31 moves drive member 20 and, in particular, stop member 26 back along the rotation axis into the axial start position. An according movement of stop member and drive member in the distal direction and back into the proximal direction is indicated by double arrow 45 in FIGS. 2 and 3.

A tooth of the rotation member which engages the next tooth of the drive member may cause an audible and/or tactile feedback to the user.

The drive mechanism is suitable for a fixed dose device or a user settable dose device. The size of the fixed dose of drug which is to delivered or the increments in which a user-settable dose may be varied by a user are preferably determined by the distribution of the teeth of the respective toothings in the drive member, rotation member and stop member. The rotation member may be rotated over more than one teeth (dose increment) of the drive member for a user-settable dose device and over one teeth (only) for a fixed dose device. The number of teeth in the drive member 20 over which the rotation member 21 rotates during dose setting determines the size of the dose which is actually delivered. The dose member and the rotation member may be adapted to one another such that the rotation member may rotate only by one tooth for a fixed dose device and by more than one tooth for a variable dose device.

Figure 4:
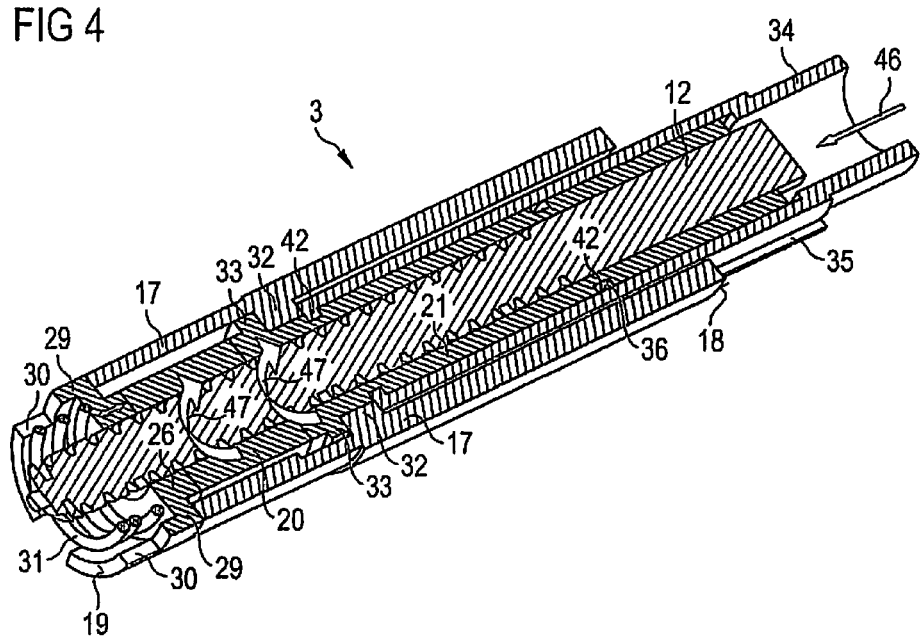
FIG. 4 schematically shows a perspective sectional view of a part of the drive mechanism according to the first embodiment with indicated movements of elements thereof during delivery of a dose.
Figure 5:
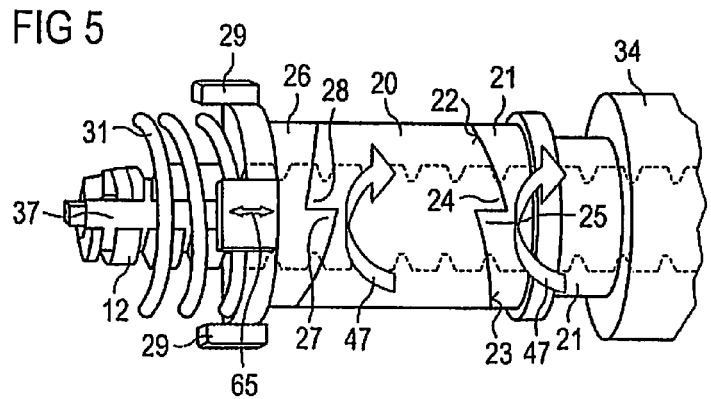
FIG. 5 schematically shows a more detailed side view of a part of FIG. 4.

After the dose has been set, the dose part 16 and with it the dose member 34 is moved (pushed) by the user in the distal direction with respect to housing part 17 (arrow 46; cf. FIGS. 4, 5). Thus, the dose member 34 is moved in the distal direction with respect to the housing part 17. The rotation member 21 accordingly rotates in the second direction, which is opposite to the first direction, with respect to the housing (arrow 47, cf. FIGS. 4, 5). Drive member 20 follows rotational movement of the rotation member in the second direction. Rotational movement of drive member 20 in the second direction is converted into rotational movement of the piston rod 12 in the second direction, which movement, in turn, is converted into movement of the piston rod 12 in the distal direction. Accordingly, the piston 10 of FIG. 1 may be displaced in the distal direction with respect to the cartridge 4 and a dose of drug 5 is dispensed from the cartridge the amount of which corresponds to the previously set dose.

During dose delivery, teeth 22 and 23 interlock and ramps of the teeth of toothing 28 of the drive member 20 slide along ramps of the teeth of toothing 27 of stop member 26. This movement is similarly as described above for the relative rotational movement of rotation member and drive member with opposite rotation direction. The stop member 26 is thereby displaced in the distal direction with respect to the drive member 20 by a distance corresponding to the depth of a tooth of toothing 27 in stop member 26. Resilient member 28 forces the stop member 26 back into the axial starting position, when the next tooth of toothing 28 is engaged by the respective tooth of toothing 27 (double arrow 65).

A tooth of the drive member which engages the next tooth of the stop member may cause an audible and/or tactile feedback to the user.

FIG. 6 illustrates the drive member 20 in greater detail in an exploded side view. The drive member 20 comprises a drive portion 200, a first coupling portion 202 and a second coupling portion 201. The drive portion 200 is arranged between the first coupling portion 202 and the second coupling 201. The drive portion 200 is coupled to the piston rod (not explicitly illustrated in FIG. 6) to transfer any rotational movement from drive member 20 onto the piston rod. Drive portion 200 comprises at each side a circumferential toothing 206, 209, e.g. formed by dog teeth. The respective toothing 209, 206 is facing a toothing 208, 209, e.g. formed by dog teeth, of the first coupling portion 202 and the second coupling portion 201, respectively. During set and dispense of a drug both toothings on each side of drive portion 200 interlock with the respective toothing of the first and second coupling portion thereby forming drive member 20. The interlocking toothings provide a bi-directional rotational coupling of the drive portion 200 with the coupling portions 201, 202 in the set and dispense mode.

In order to facilitate interlocking, the respective toothing 206, 209 of the drive portion may comprise rectangular protrusions 230 which are arranged opposite to corresponding recesses 231 in the respective coupling portion. Protrusion 230 and recesses 231 engage to interlock the drive portion 200 with the coupling portions 201, 202.

In the set and dispense mode the resilient member 31 exerts a force onto stop member 26 and drive member 20. In the set and dispense mode all three portions 200, 201 and 202 of drive member 20 are engaged and bi-directionally rotationally coupled to each other such that drive member 20 operates as illustrated above in conjunction with the previously described embodiments.

For resetting the drug delivery device, e.g. when an empty cartridge should be substituted with a new one, the drive portion is decoupled from the coupling portions such that the drive portion may be rotated in the first direction with respect to the housing, i.e. that direction in which rotation was previously prevented due to the coupling between the first coupling portion 202 and the stop member 26 and the coupling of the drive portion with the coupling portions. For decoupling the drive portion from the coupling portions, the force which tends to keep the drive member 20 in engagement with the stop member 26 and the rotation member 21 is reduced, for example by detaching the cartridge retaining member 11 which may counteract the force exerted by the resilient member 31. In particular, the resilient member 31 may then be permitted to relax. As a result, the first and second coupling portion 201 and 202 disengage from the drive portion 200 of drive member 20 by a movement caused by two further resilient members 203 and 204.

The first resilient member 204 is arranged between the first coupling portion 202 and the drive portion 200 and disengages them from each other. Thus, the first coupling portion, the stop member 26 and the drive portion 200 may be displaced relative to each other driven by resilient member 204 such that the drive portion 200 and the first coupling portion 202 are disengaged. The second resilient member 203 is arranged between drive portion 200 and second coupling portion 201. Thus, the second coupling portion 201, the rotation member 21 and/or the drive portion may be displaced relative to each other driven by resilient member 203 such that the drive portion 200 and the second coupling portion 201 are disengaged. The first coupling portion 202 may stay in abutment with the stop member 26 and the second coupling portion 201 may stay in abutment with the rotation member 21 while the drive portion 200 is decoupled from both coupling portions 201, 202.

In the set and dispense mode, the force exerted by the resilient member 31 is sufficient to overcome the forces exerted by resilient members 203, 204, which tend to decouple the drive portion from the coupling portions 201, 202. Therefore, the drive portion is coupled to the coupling portions 201, 202 in the set and dispense mode of operation. Thus, in the set and dispense mode, all portions of the drive member 20 rotate as if the drive member was a single member and not a multi-part member. No significant relative movement can occur between those portions. In the reset mode, the resilient members 203, 204 separate the drive portion 200 from the coupling portions 201, 202. Thus, relative rotation of the drive portion 200 with respect to the coupling portions 201, 202 is permitted in the reset mode.

Expediently, the drive portion 200 is the only portion of the drive member 20 which is coupled, e.g. splined, to the piston rod (not explicitly shown, see FIGS. 1 to 5). Thus, for resetting the piston rod back to an initial starting position, the drive portion 200 may rotate in the first direction with respect to the housing and with respect to the coupling portions 201, 202, which is converted into proximal movement of the piston rod with respect to the housing.

The respective resilient member 203, 204 may be a separate member, e.g. a coil spring, a wave spring, a wavy washer, an elastomeric component, a metal component, or a plastic hinge. Alternatively, the respective resilient member 203, 204 may be integrated in the drive portion or the respective coupling portion.

Figure 7:
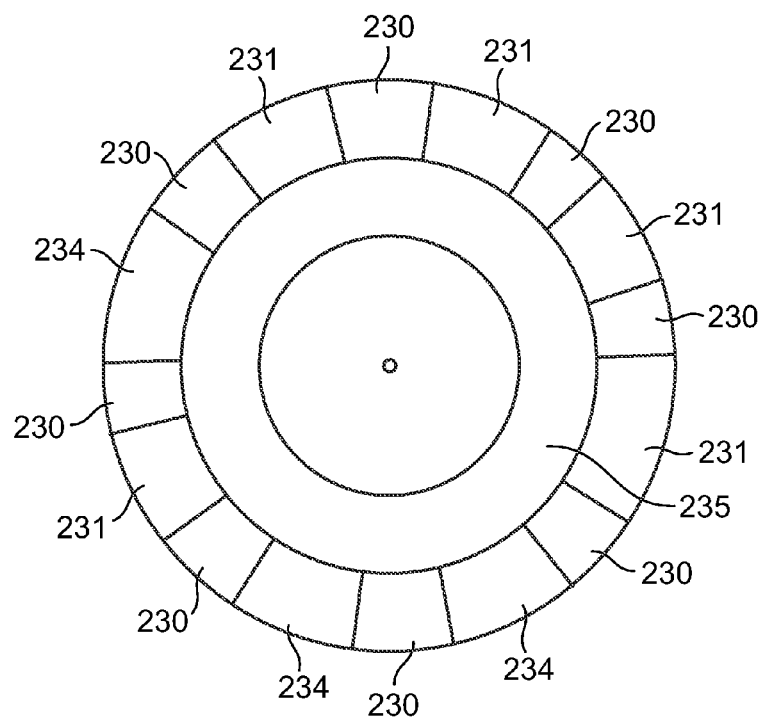
FIG. 7 illustrates a top view on an exemplary embodiment of the drive portion.

FIG. 7 illustrates a top view on drive portion 200. Protrusions 230 and the adjacent recesses 231 are arranged circumferentially around the drive portion 200. An inwardly directed shoulder 235 is provided inside of drive member 200. Shoulder 235 may be used as a support for the resilient members 204 and 203, respectively.

With the resettable drive mechanisms described herein above a good dose accuracy may be achieved. The drive mechanisms are for example but not limited thereto suitable for dispensing doses of the drug from and including 1 IU up to and including 30 IU, preferably from and including 3 IU up to and including 20 IU. Also, doses of 30 IU or more or 1 IU or less may be dispensed by means of the described drive mechanisms. However, doses of from and including 1 IU up to and including 30 IU are particularly suitable. For example, if a device described in conjunction with FIGS. 1 to 6, in which the piston rod rotates during displacement, was to be designed for doses less than 1 IU, the thread of the piston rod should have a low pitch and/or the number of teeth of the respective toothing of drive member and rotation member should be increased. Of course, the production costs may increase on account of the finer segmentation of the toothings and the lower pitch thread. In order to provide for a device configured to deliver doses greater than 30 IU, e.g. 50 IU or greater, the thread in the piston rod should have a higher pitch. Consequently, small deviations from a predetermined course of the thread result in major absolute deviations from the desired dose. Thus, the risk of a reduction in dose accuracy may be increased. In addition, the risk of self-locking of a threaded engagement may be increased.

A diameter of the outer housing of the drug delivery device may be less than or equal to 20 mm, preferably less than or equal to 16 mm, particularly preferably less than or equal to 14 mm.

The invention claimed is:

1. A drive mechanism for a drug delivery device, comprising:
   a housing having a proximal end and a distal end;
   a piston rod, which is adapted to be displaced in a distal direction with respect to the housing when dispensing a drug dose;
   a drive member which is adapted to be rotated when dispensing the drug dose, wherein the drive mechanism is configured to convert rotational movement of the drive member into a movement of the piston rod in the distal direction with respect to the housing;
   a stop member which is adapted to prevent a rotational movement of the drive member with respect to the housing when setting a drug dose;
   wherein the drive member comprises a drive portion being coupled to the piston rod and a first coupling portion which couples the drive portion and the stop member, wherein the drive mechanism is configured to be switchable between a set and dispense mode of operation and a reset mode of operation, and wherein, in the set and dispense mode, said first coupling portion is bi-directionally coupled to the drive portion for setting and dispensing the drug dose, and wherein, in the reset mode, said first coupling portion is decoupled from the drive portion to allow a reset operation to be performed for the drive mechanism.

2. The drive mechanism according to claim 1, wherein, in the set and dispense mode, the first coupling portion is coupled to the stop member by a uni-directional friction clutch mechanism, which is configured to prevent relative rotational movement between the stop member and the first coupling portion when setting the drug dose and to permit relative rotational movement between the stop member and the first coupling portion when dispensing the drug dose.

3. The drive mechanism according to claim 1, wherein the first coupling portion and the drive portion each comprise an interlocking element, said interlocking elements facing each other.

4. The drive mechanism according to claim 1, the drive member further comprising:
a first resilient member arranged between the first coupling portion and the drive portion, said first resilient member being adapted to axially displace one of the first coupling portion and the drive portion with respect to the other one of the first coupling portion and the drive portion.

5. The drive mechanism according to claim 1, further comprising:
a rotation member, which is, in the set and dispense mode, adapted to be rotated in a first direction with respect to the housing when setting the drug dose and to be rotated in a second direction with respect to the housing when dispensing the drug dose, said second direction being opposite to the first direction, wherein, in the set and dispense mode, the drive member is adapted to follow the rotational movement of the rotation member when dispensing the drug dose.

6. The drive mechanism according to claim 5, wherein the drive member (20) further comprises:
a second coupling portion arranged between the drive portion and the rotation member, wherein, in the set and dispense mode, said second coupling portion is bi-directionally coupled to the drive portion and is disengaged from the drive portion in the reset mode of the drive mechanism.

7. The drive mechanism according to claim 5, wherein the drive member is coupled to the rotation member by a uni-directional friction clutch mechanism, which is configured to permit relative rotational movement between rotation member and the drive member during rotation of the rotation member in the first direction for setting the drug dose and to prevent relative rotational movement of the rotation member and the drive member during rotation of the rotation member in the second direction for dispensing the dose.

8. The drive mechanism according to claim 6, wherein the second coupling portion and the drive portion each comprise an interlocking element, said interlocking elements facing each other.

9. The drive mechanism according to claim 6, the drive member further comprising:
a second resilient member arranged between the second coupling portion and the drive portion, said second resilient member being adapted to axially displace one of the second coupling portion and the drive portion with respect to the other one of the second coupling portion and the drive portion.

10. The drive mechanism according to claim 4, wherein the first and/or the second resilient members each comprise at least one of the following:
a coil spring,
a wave spring,
a wavy washer,
an elastomeric component,
a metal component,
a plastic hinge
wherein the first and/or the second resilient member exerts an axial force when deformed.

11. The drive mechanism according to claim 4, wherein at least one of the first and second resilient member is integrated in the respective coupling portion or in the drive portion.

12. The drive mechanism according to claim 1, further comprising:
a resilient element exerting an axially directed force onto the stop member and the drive member to hold them in abutment when setting and dispensing the drug dose.

13. The drive mechanism according to claim 1, wherein the stop member and/or the rotation member is movable in axial direction with respect to the housing when switching the drive mechanism into the reset mode.

14. The drive mechanism according to claim 1, wherein the drive portion is, preferably permanently, engaged with the piston rod in the set and dispense mode and in the reset mode and the first coupling portion and, if applicable, the second coupling portion are disengaged from the piston rod in the set and dispense mode and in the reset mode.

15. A drug delivery device comprising the drive mechanism according to claim 1 and a replaceable cartridge, the cartridge holding a plurality of doses of the drug (5).

16. The drug delivery device according to claim 15, wherein the replaceable cartridge is removably arranged, and wherein the first coupling portion is disengaged from the drive portion for resetting the drive mechanism when the cartridge is removed from the drug delivery device.

17. The drug delivery device according to claim 15, wherein the second coupling portion is disengaged from the drive portion for resetting the drive mechanism when the cartridge is removed from the drug delivery device.

* * * * *